(12) United States Patent
Kalantar-Zadeh et al.

(10) Patent No.: US 7,027,921 B2
(45) Date of Patent: Apr. 11, 2006

(54) SURFACE ACOUSTIC WAVE SENSOR

(75) Inventors: Kourosh Kalantar-Zadeh, Melbourne (AU); Wojtek Wlodarski, Melbourne (AU)

(73) Assignee: Microtechnology Centre Management Limited, Victoria (AU)

( * ) Notice: Subject to any disclaimer, the term of this patent is extended or adjusted under 35 U.S.C. 154(b) by 49 days.

(21) Appl. No.: 10/477,951

(22) PCT Filed: May 20, 2002

(86) PCT No.: PCT/AU02/00616

§ 371 (c)(1),
(2), (4) Date: Nov. 18, 2003

(87) PCT Pub. No.: WO02/095940

PCT Pub. Date: Nov. 28, 2002

(65) Prior Publication Data

US 2004/0133348 A1    Jul. 8, 2004

(30) Foreign Application Priority Data

May 21, 2001 (AU) .................................. PR 5076

(51) Int. Cl.
*G01N 29/02* (2006.01)

(52) U.S. Cl. ..................... 702/2; 310/313 R

(58) Field of Classification Search ........... 702/1–6; 73/579; 310/360, 313 A, 313 R; 436/501, 436/151; 422/82.01; 428/336
See application file for complete search history.

(56) References Cited

U.S. PATENT DOCUMENTS

| | | | | |
|---|---|---|---|---|
| 4,454,440 A | * | 6/1984 | Cullen | 310/313 R |
| 4,562,371 A | * | 12/1985 | Asai et al. | 310/313 A |
| 4,672,254 A | * | 6/1987 | Dolat et al. | 310/313 R |
| 5,130,257 A | * | 7/1992 | Baer et al. | 436/151 |
| 5,216,312 A | * | 6/1993 | Baer et al. | 310/313 D |
| 5,283,037 A | * | 2/1994 | Baer et al. | 422/82.01 |
| 5,321,331 A | * | 6/1994 | Baer et al. | 310/313 D |
| 5,364,797 A | * | 11/1994 | Olson et al. | 436/501 |
| 5,432,392 A | | 7/1995 | Kadota et al. | 310/313 A |
| 5,453,652 A | * | 9/1995 | Eda et al. | 310/313 R |
| 5,705,399 A | * | 1/1998 | Larue | 436/501 |
| 5,847,486 A | | 12/1998 | Kadota et al. | 310/313 R |
| 5,888,646 A | * | 3/1999 | Takahashi et al. | 428/336 |
| 6,121,713 A | | 9/2000 | Inoue et al. | 310/313 A |
| 6,378,370 B1 | * | 4/2002 | Haskell et al. | 73/579 |

FOREIGN PATENT DOCUMENTS

| | | |
|---|---|---|
| JP | 11097973 | 4/1999 |
| JP | 11136082 | 5/1999 |

OTHER PUBLICATIONS

DRAFTS, Sensors, "Acoustic wave technology sensors", Oct. 2000, Retrieved from the Internet on Jun. 19, 2002: URL: www.sensormag.com/articles/100/68/main.stml.

* cited by examiner

*Primary Examiner*—Bryan Bui
*Assistant Examiner*—Victor J. Taylor
(74) *Attorney, Agent, or Firm*—Connolly Bove Lodge & Hutz LLP

(57) ABSTRACT

A surface acoustic wave sensor is provided having a piezoelectric material deposited on a piezoelectric substrate. The preferred structure is zinc oxide on ST-cut quartz crystals that allows propagation of a Love mode acoustic wave end is particularly useful in liquid media as well as gas. The sensor can be used to detect biological or chemical moieties.

3 Claims, 5 Drawing Sheets

SURFACE ACOUSTIC WAVE SENSOR

PRIORITY REFERENCE

Priority is based on Australian Application PR 5076 filed May 21, 2001.

FIELD OF THE INVENTION

This invention relates to improvements in Surface Acoustic Wave [SAW] devices and particularly SAW devices used as sensors.

BACKGROUND OF THE INVENTION

SAW devices have been used as sensors in liquid and gaseous environments. U.S. Pat. No. 4,562,371 discloses a SAW device comprising a ZnO piezo layer on a cut crystalline silicon substrate that propagates Rayleigh waves.

The surface acoustic waves propagate in 3 directions and can be classified as longitudinal wave motion, Normal waves or shear horizontal waves. A class of shear horizontal [SH] waves are called Love waves which are propagated in layered devices that concentrate the wave energy in a highly confined region near to the surface.

Rayleigh wave sensors have been useful in gaseous environments but they are not suitable for liquid environments because the surface-normal displacement causes strong radiative loss into the liquid. For sensing in liquids shear horizontal [SH] polarised wave modes are preferred since the particle displacement is parallel to the device surface and normal to the direction of propagation. This allows a wave to propagate in contact with a liquid without coupling excessive acoustic energy into the liquid. However the SH wave is distributed through the substrate and therefore does not have the same sensitivity as the SAW. For increased sensitivity Love waves which are SH-polarised guided surface waves may be used. The waves propagate in a layered structure consisting of a piezoelectric substrate and a guiding layer which couples the elastic waves generated in the substrate to the near surface. They are extremely sensitive to surface perturbations due to the energy confinement to the near surface. By observing the magnitude of perturbations it is possible to measure the strength of the interaction. The interactions may be caused by mass density, elastic stiffness, liquid viscosity, electric and dielectric properties. The more sensitive is the device the smaller the quantities that can be measured.

U.S. Pat. Nos. 5,130,257, 5,216,312, 5,283,037 and 5,321,331 disclose love mode SAW sensors used in liquid environments. The love waves are produced by cutting the piezo electric material such as lithium niobate, lithium tantalate or quartz to couple energy from the interdigital transducers [IDT's] of the SAW device into shear transverse or love waves that enable the wave energy to be trapped at the substrate surface.

U.S. Pat. No. 5,705,399 discloses a SAW sensor for liquid environments having an AT cut quartz piezo substrate with electrodes connected to a first side in contact with a liquid and a second side that is not in contact. The sensor may be used to detect biological species such as antigens.

U.S. Pat. No. 5,364,797 discloses the use of a porous material as a surface layer of high surface area for SAW devices.

Porous surfaces are used in gaseous environments to increase the contact surface area and consequently the sensitivity of the device. Porous surface have not been used in liquid media because the porous surface increases viscosity which leads to insertion losses and decreasing sensitvity.

It is an object of this invention to improve the sensitivity of SAW sensors particularly in liqid media.

BRIEF DESCRIPTION OF THE INVENTION

To this end the present invention provides a surface acoustic wave sensor which includes a piezoelectric layer on a piezoelectric substrate.

Preferably the piezoelectric substrate is cut for propagation of love mode waves.

Preferably the piezoelectric layer is porous.

This structure provides the following advantages:
1—High Electromechanical Coupling Coefficient ($K^2$).
2—Small Temperature Coefficient.
3—High confinement of energy on the surface.
4—Ability of the device to operate in liquid media with a porous surface.

The Piezo substrate may be quartz crystal, lithium Niobate [$LiNbO_3$] or lithium tantalate [$LiTaO_3$].

A preferred piezo substrate is 90° rotated ST-cut quartz crystal which has a propagation speed of 5000 m/s and the dominant wave is SSBW and has zero coupling to other modes. It is dominantly a Shear Horizontal [SH] bulk wave and has a low temperature coefficient. Its major disadvantage is a high insertion loss as it changes from SSBW to love mode. When a film material is deposited on the surface it should load the substrate which means the speed of propagation in the film is less than in the substrate. In this case the mode of propagation changes to love mode. When metal oxides films are deposited on the substrate the insertion loss is decreased as the mode of operation changes from SSBW to Love mode. Its main advantage is a lower insertion loss as it decreases from SSBW to Love mode.

The preferred porous piezoelectric material is a layer of zinc oxide which is a porous surface formed by hexagonal pillars. ZnO is the best candidate for fabricating Love mode devices. It has a porous surface and is a piezoelectric material with a low phase velocity (2650 m/s). This implies that ZnO can increase the electromechanical coupling coefficient more than other deposited materials. Furthermore, ZnO consists of hexagonally shaped cylinders with gaps in between them, making the guiding layer porous. ZnO has a positive temperature coefficient whereas 90° rotated ST-cut quartz crystal has a negative temperature coefficient.

The combination of positive and negative temperature coefficients assists to is reduce the temperature coefficient of the whole structure. Around room temperature (25° C.) the temperature coefficient remains relatively lower than that of the blank SSBW structures.

A biologically sensitive layer may be deposited on the piezo layer to interact with the appropriate biochemical components to be detected. A gold film may be deposited on the surface. Gold interacts with high affinity to proteins. It can be used with specific antibodies for antigen detection. This deposit can be made on a porous surface as well as a smooth surface.

In a further aspect the present invention provides a sensor for use in detecting chemical or biochemical moieties in gaseous or liquid mediums which incorporates a surface acoustic wave device which consisting of
a substrate of a piezoelectric quartz crystal
at least one interdigital transducer formed on said quartz crystal a piezoelectric film of zinc oxide deposited on said crystal and transducer a biologically sensitive layer deposited on said zinc oxide layer An important advantage of the present invention is the sensitivity of of the sensor. The mass detection limit is 100 pg/cm$^2$ which is at least 10 times more sensitive than sensors using other substrates and 2 to 3 times more sensitive than quartz crystals with a non piezo layer such as $SiO_2$.

DETAILED DESCRIPTION OF INVENTION

This invention provides piezoelectric layers on piezoelectric substrates. The Substrate's cut belongs to a class of crystal cuts that support Surface Skimming Bulk Wave (SSBW). The layers are of different of piezoelectric materials that can be deposited as a highly directional film on the substrate, which let acoustic waves propagate on shear horizontal direction. Speed of propagation of acoustic wave in the layers must be less than the substrate to support Love mode of propagation.

Figure 1:
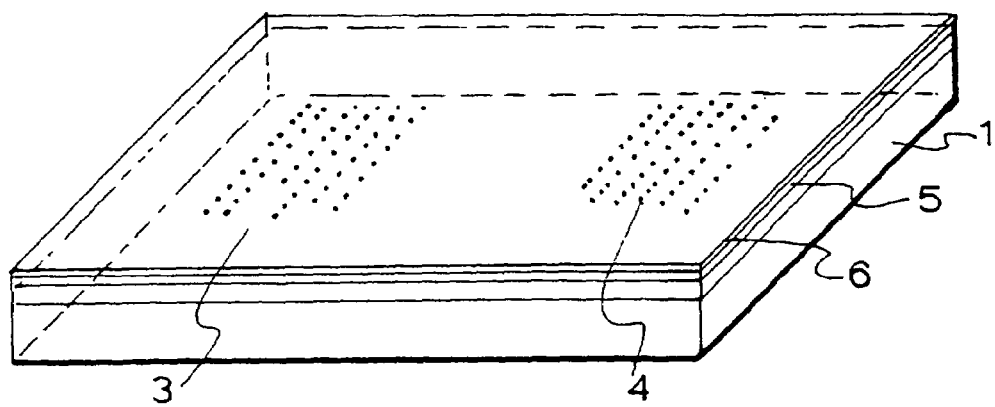
FIG. 1 is a schematic illustration of a SAW device of this invention.

In FIG. 1 a first wave generating transducer 3 and a first receiving transducer 4 are fabricated onto the surface of a piezoelectric substrate 1. The transducers 3 and 4 are any suitable interdigital transducer used in SAW devices. The wave transmitting layer 5, a porous piezoelectric layer, is fabricated onto the substrate 1 such that the transducers 3 and 4 lie between the substrate 1 and the layer 5.

A sensing layer 6 is deposited on to the wave propagation layer 5 to form a surface which is physically, chemically or biologically active, selectively to agents in the liquid or gaseous media to which the surface 6 is exposed.

Figure 2:
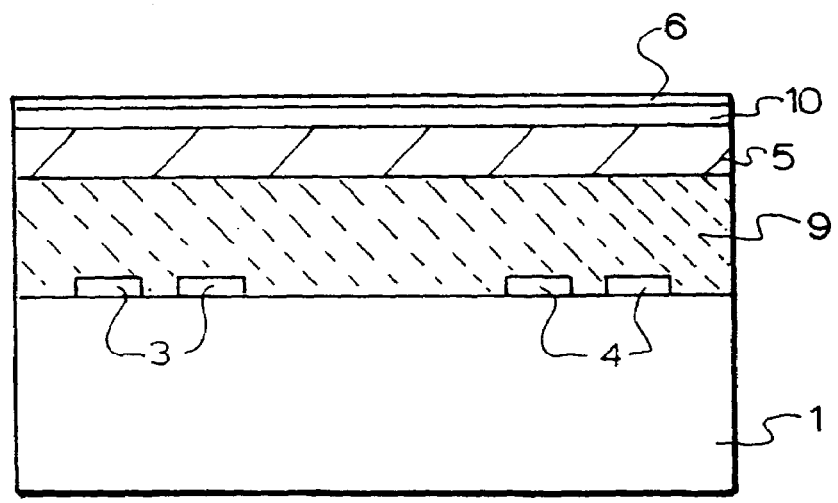
FIG. 2 is a cross section of another embodiment of the invention.

FIG. 2 is a cross sectional view of another embodiment similar to that of FIG. 1 except that a transitional layer 9 and a protecting layer 10 are also included. The transitional layer 9 is preferably an acoustically sensitive layer such as $SiO_2$ which increases the velocity shift and as a result increases the electromechanical coupling factor. The transition layer 9 lies between the wave transmitting layer 5 and the substrate 1 so that the distance between the first IDT and layer 5 is increased to facilitate a higher coupling coefficient and reduce the acoustic wave transmission energy loss which otherwise occur. The protective layer 10 lies between the sensing layer 6 and the piezo layer 5 to protect layer 5 from damage.

The protective layer 10 may also be $SiO_2$.

Figure 3:
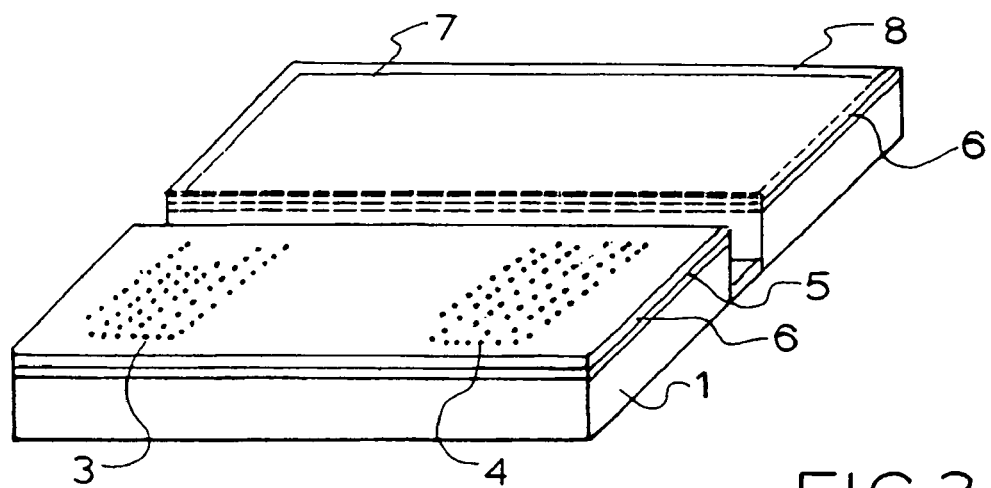
FIG. 3 is a perspective view of a further embodiment including a second set of wave generating and receiving acoustic transducers.

In FIG. 3 a second wave generating transducer 7 and a second receiving transducer 8 above the substrate layer and below the wave transmitting layer and near the first generating transducers 3 and receiving transducers 4. Both sets of transducers may be located on substrate 1 or the second set may be on a separate substrate. It is preferred that no sensing layer is located above the second set of transducers 7 and 8 so that they can function as a reference sensor.

Figure 4:
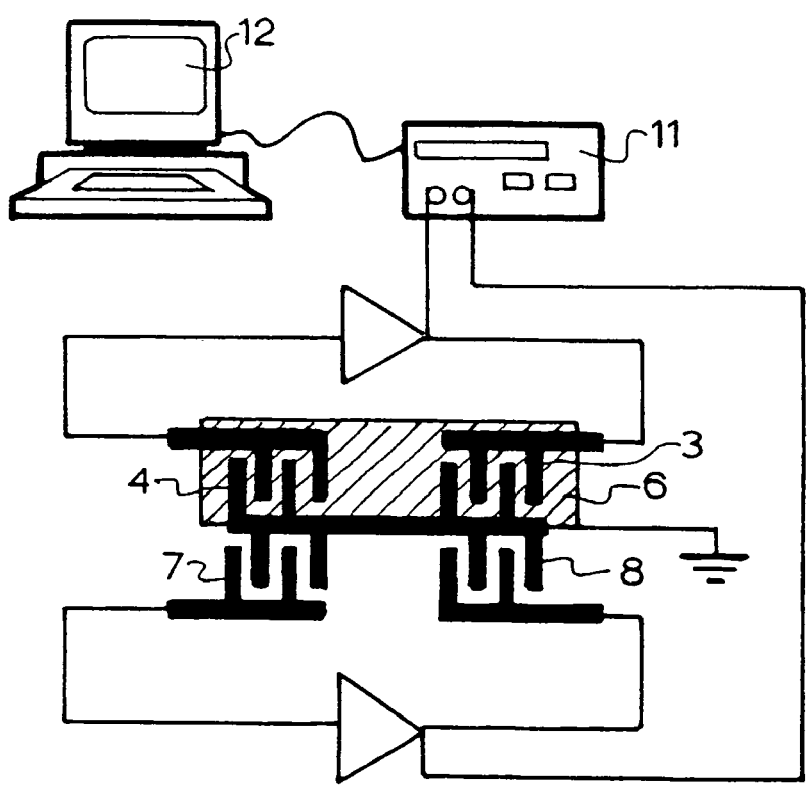
FIG. 4 is a schematic illustration of a preferred sensor and analyser of this invention.

In FIG. 4 the SAW device of this invention is shown in a detector device. A frequency counter 11 determines frequency of the output signals and a computing device 12 calculates the concentration of the detectable components in the liquid or gaseous media. The output from the first receiver transducer 4 contains the sensing signal which is a consequence of the interaction between the sensing layer and the target molecules. The output from the second receiving transducer 8 contains only the operational characteristics of the sensing device because thee is no sensing layer 6 above it. This enables the analyser to compute accurately a signal indicative of the concentration of the target molecule.

The piezoelectric substrate must support SSBW mode of operation. A few examples of suitable piezoelectric materials are shown in table 1.

TABLE 1

Some Piezoelectric Crystals Suited to Surface Skimming Bulk Wave (SSBW) Propagation

| Piezoelectric | Euler angle $\phi$ | Euler angle $\theta$ | Euler angle $\psi$ | SSBW Velocity (m/s) |
|---|---|---|---|---|
| 90° rotated ST-Cut Quartz | 0 | 132.75 | 90 | 4990 |
| 35.5° AT-cut quartz | 0 | 125.15 | 90 | 5100 |
| 36° rotated YX-LiTaO$_3$ | 0 | 36 | 0 | 4221 |
| 37° rotated LiNbO$_3$ | 0 | 37.93 | 0 | 4802 |

The surface film must be a piezoelectric. A few examples piezoelectric films are shown in table 2.

TABLE 2

| | Piezoelectric films | |
|---|---|---|
| Material | Most Common Deposition methods * | Structure ** |
| CdS | VE | PC |
| ZnO | CVD, RF-MSP | SC, PC |
| Bi12PbO19 | RF-SP | PC |
| AlN | RF-SP, CVD | SC/PC |

* VE (Vacuum Evaporation), CVD (Chemical Vapour Deposition), (Radio Frequency Magnetron Sputtering), RF-SP (Radio Frequency Sputtering)
** PC (Poly crystal), SC (Single Crystal)

EXAMPLE 1

A dual line ZnO/90° rotated ST-Cut Quartz crystal structure is fabricated with a ZnO layer ranging from 0 to 3.2 microns. A 15 nm Cr(5 nm)/Au(12 nm) layer is deposited as the sensitive layer over one of the delay lines. Cr/Au grows along the ZnO cylinders which increases the sensing surface of the gold.

Coupling coefficient, temperature coefficient velocity, insertion loss have been studied as a function of layer thickness. Magnitudes have been compared with $SiO_2$/90° rotated ST-cut quartz crystal structure. The love wave transducers are fabricated on 0.5 mm thick 90° rotated ST-cut quartz crystal wafers. The transmit and receive IDT's consisted of 64 and 16 finger pairs in input and output ports respectively. The utilised acoustic wavelength is 50 microns. The acoustic centre to centre distance of transmitting and receiving IDT's is 60 wavelengths and aperture was chosen as 50 wavelengths.

ZnO films of different thicknesses were deposited by a r.f. magnetron sputterer.

ZnO is a piezoelectric material of hexagonal crystalline structure. It is a wurtzite type crystal with a 6 mm symmetry. Layers occupied by zinc atoms alternate with layers occupied by oxygen atoms. The effective ionic charges are about 1 to 1.2 which results in polar c axis.

The epitaxial growth of ZnO films is influenced by deposition rate, substrate temperature, sputtering gas pressure and target configuration.

Table 3 illustrates the conditions of epitaxial ZnO film on ST-cut quartz crystal wafers.

TABLE 3

| Target substrate distance | 5 cm |
| --- | --- |
| Sputtering gas combination | Ar 60% + $O_2$ 40% |
| Sputtering gas Pressure | 0.01 torr |
| Substrate temperature | 270° C. |
| RF power | 40 W |
| Deposition rate | 0.64 micron/h |

Figure 5:
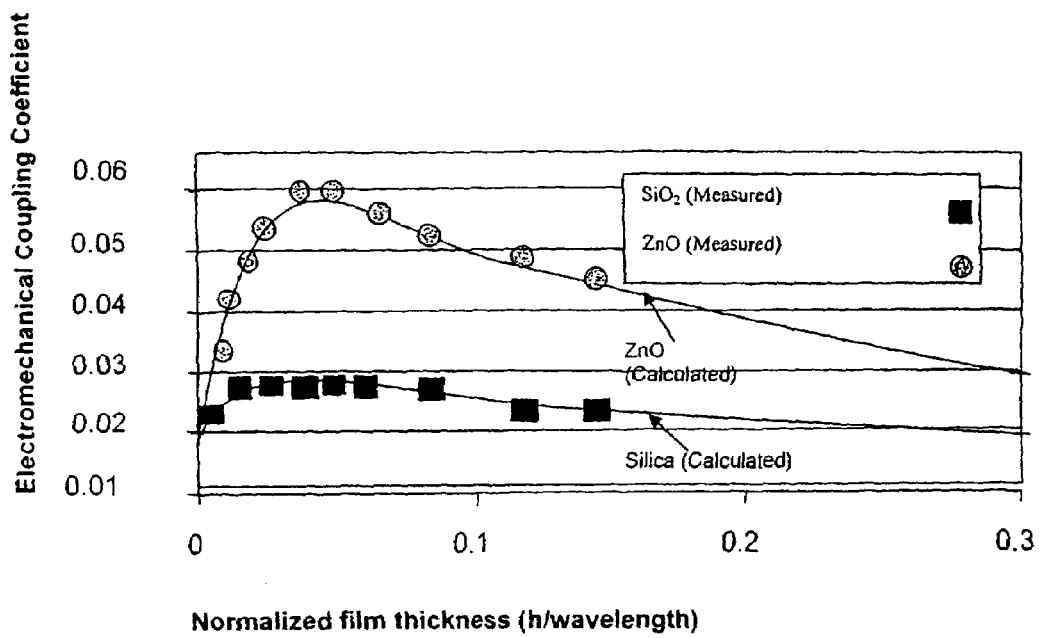
FIG. 5 is a comparison of the coupling coefficient for ZnO and $SiO_2$ films on an ST-cut quartz crystal wafer.

The film deposited at 270° C. showed a resistivity as high as $5 \times 10^6$ ohm/cm. Electro mechanical coupling coefficients for ZnO and $SiO_2$ films on ST-cut quartz wafers are shown in FIG. 5.

EXAMPLE 2

Figure 6:
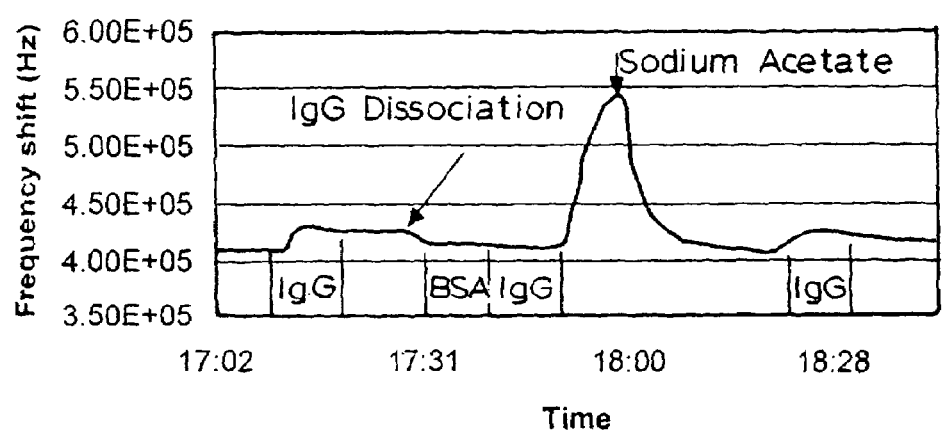
FIG. 6 illustrates the response of the sensor of this invention to a sequence of different solutions.

An example of the response of the system to a sequence of different solutions is shown in FIG. 6.

The sensitive layer is gold. A flow of IgG (Immuno-Globulin G, 10 ng/ml) and BSA (Bovine Serum Albumin, 0.01 mg/ml) in 7.4 pH buffer pumped into the liquid cell with a flow rate of 0.05 ml/minute.

With the purge of IgG solution in buffer, IgG particles are adsorb to Au surface. It causes a frequency shift of about 4 KHz. Then the flow of buffer continues till all IgG dissociate from the surface. Afterwards, BSA is used to cover the Au surface and the surface of the reference transducer. By covering the sensitive layer there will be no adsorption and response occurs with another flow of IgG solution. Afterwards, Au surface was cleaned with a purge of Sodium Acetate solution. Then IgG solution liquid would be pumped and there will be the same frequency shift due to the adsorption of IgG particles on the Au surface. It shows the experiment is repeatable and only responds to the selective layer.

Other methods that can be used for protein immobilization are:
1—The physical adsorption onto the selective layer
2—Covalent binding to the selective layer
3—Adsorption into polymeric selective layers
4—Inclusion in a polymer lattice
5—Inclusion by sheeting with a membrane
6—Cross-linking a co-polymerization with either di-functional or poly-functional chemical reactive monomers.

EXAMPLE 3

For gas sensing experiments, the thickness of the ZnO layer was 2.8 µm giving an operational frequency of 90 MHz for the periodicity of 50 µm. The sensor was heated to 350° C. by a micro-heater located beneath the device.

Figure 7:
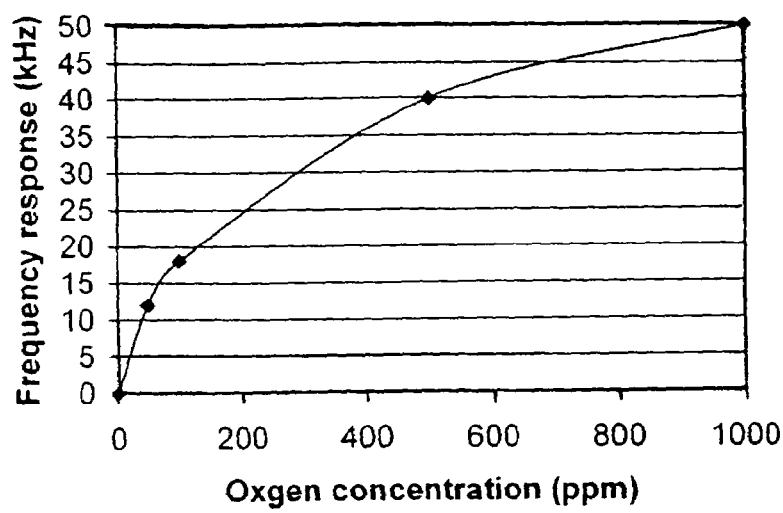
FIG. 7 illustrates the response of the sensor of this invention to a sequence of 100 ppm $O_2$ in $N_2$.

The sensor was exposed to different concentrations of oxygen in nitrogen gas to investigate the response the Love mode SAW sensor. The response to 100 ppm of oxygen in nitrogen is shown in FIG. 7. Exposing the device to oxygen gas increases the operational frequency of the system. This increase in frequency is almost +18 kHz. For oxygen, the response and recovery times are continuous which stand for a single reaction on the surface.

Figure 8:
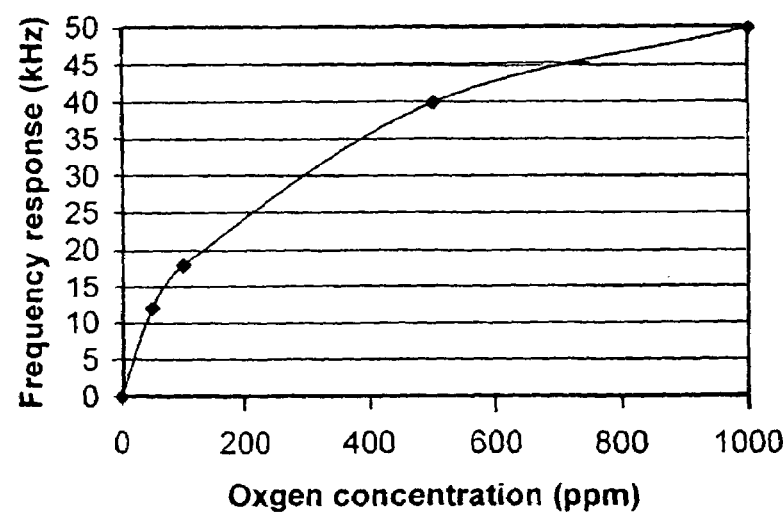
FIG. 8 illustrates the frequency shift of the sensor of this invention exposed to different oxygen concentrations.
Figure 9:
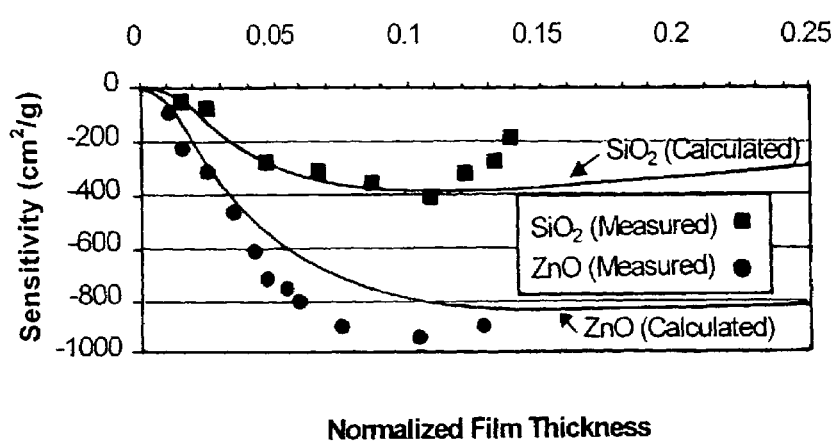
FIG. 9 is a plot that illustrates sensor sensitivity as a function of normalized film thickness for ZnO and $SiO_2$ films.

The response of the sensor to different oxygen concentrations is shown in FIG. 8. The response of the sensor to 50 ppm is equal to −11 kHz. If the response from this point onward would continue to be linear, then the response of the device to 0.5 ppm will be equal to 110 Hz. The noise of the system is approximately 50 Hz in the gas media.

From the above it can be seen that this invention provides a unique sensor structure with significant advantages. Those skilled in the art of biological sensing will realise that the sensor of this invention can be adapted to detect a wide variety of biological or chemical moieties in both liquid and gaseous media.

The invention claimed is:

1. A sensor for use in detecting chemical or biochemical moieties in gaseous or liquid mediums which incorporates a surface acoustic wave device comprising:
   a substrate of a piezoelectric 90° rotated ST-cut quartz crystal cut;
   at least one inter-digital transducer formed on said quartz crystal;
   a piezoelectric film of zinc oxide deposited on said crystal and transducer; and a biologically sensitive layer, adapted to interact with an appropriate biochemical component to be detected, deposited on said zinc oxide layer.

2. A sensor as claimed in claim 1 in which the biologically sensitive layer comprises a protein adsorbed on a layer of gold.

3. A sensor as claimed in claim 1 in which the quartz crystal substrate and the zinc oxide coating are fabricated for propagating a Love mode surface acoustic wave.

* * * * *